(12) United States Patent
Burgermeister et al.

(10) Patent No.: US 8,080,052 B2
(45) Date of Patent: Dec. 20, 2011

(54) STENT WITH DIAGONAL FLEXIBLE CONNECTING LINKS

(75) Inventors: Robert Burgermeister, Bridgewater, NJ (US); David C. Majercak, Stewartsville, NJ (US); David R. Fischell, Fair Haven, NJ (US); Hikmat Hojeibane, Princeton, NJ (US); Robert E. Fischell, Dayton, MD (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

(21) Appl. No.: 10/185,250

(22) Filed: Jun. 28, 2002

(65) Prior Publication Data
US 2004/0002753 A1   Jan. 1, 2004

(51) Int. Cl.
*A61F 2/82* (2006.01)
(52) U.S. Cl. ...................... 623/1.15; 623/1.16
(58) Field of Classification Search .................. 623/1.15
See application file for complete search history.

(56) References Cited

U.S. PATENT DOCUMENTS

| | | | | | |
|---|---|---|---|---|---|
| 5,807,404 | A | * | 9/1998 | Richter | 623/1.16 |
| 6,129,755 | A | * | 10/2000 | Mathis et al. | 623/1.15 |
| 6,136,023 | A | * | 10/2000 | Boyle | 623/1.22 |
| 6,190,403 | B1 | | 2/2001 | Fischell et al. | |
| 6,409,761 | B1 | * | 6/2002 | Jang | 623/6.12 |
| 6,669,722 | B2 | * | 12/2003 | Chen et al. | 623/1.15 |
| 2002/0072792 | A1 | | 6/2002 | Burgermeister et al. | |
| 2002/0123799 | A1 | | 9/2002 | Burgermeister | |

FOREIGN PATENT DOCUMENTS

| | | |
|---|---|---|
| EP | 0 884 029 A | 12/1988 |
| EP | 0 830 853 A | 3/1998 |
| EP | 1 212 991 A | 6/2002 |
| FR | 2 813 785 A | 3/2002 |
| GB | 2 369 062 A | 5/2002 |
| WO | WO 00/30563 | 6/2000 |
| WO | WO 02/24111 A | 3/2002 |

* cited by examiner

*Primary Examiner* — Thomas J Sweet
*Assistant Examiner* — Christopher D Prone

(57) ABSTRACT

The present invention envisions an improved flexible connecting link used in conjunction with in-phase and half-phase circumferential sets of strut members. By increasing the total length and diagonality of the undulating connecting links, the present invention is a stent that provides increased flexibility during delivery and enhanced conformability to the shape of a curved artery when the stent is deployed into a curved vessel such as a tortuous coronary artery.

11 Claims, 8 Drawing Sheets

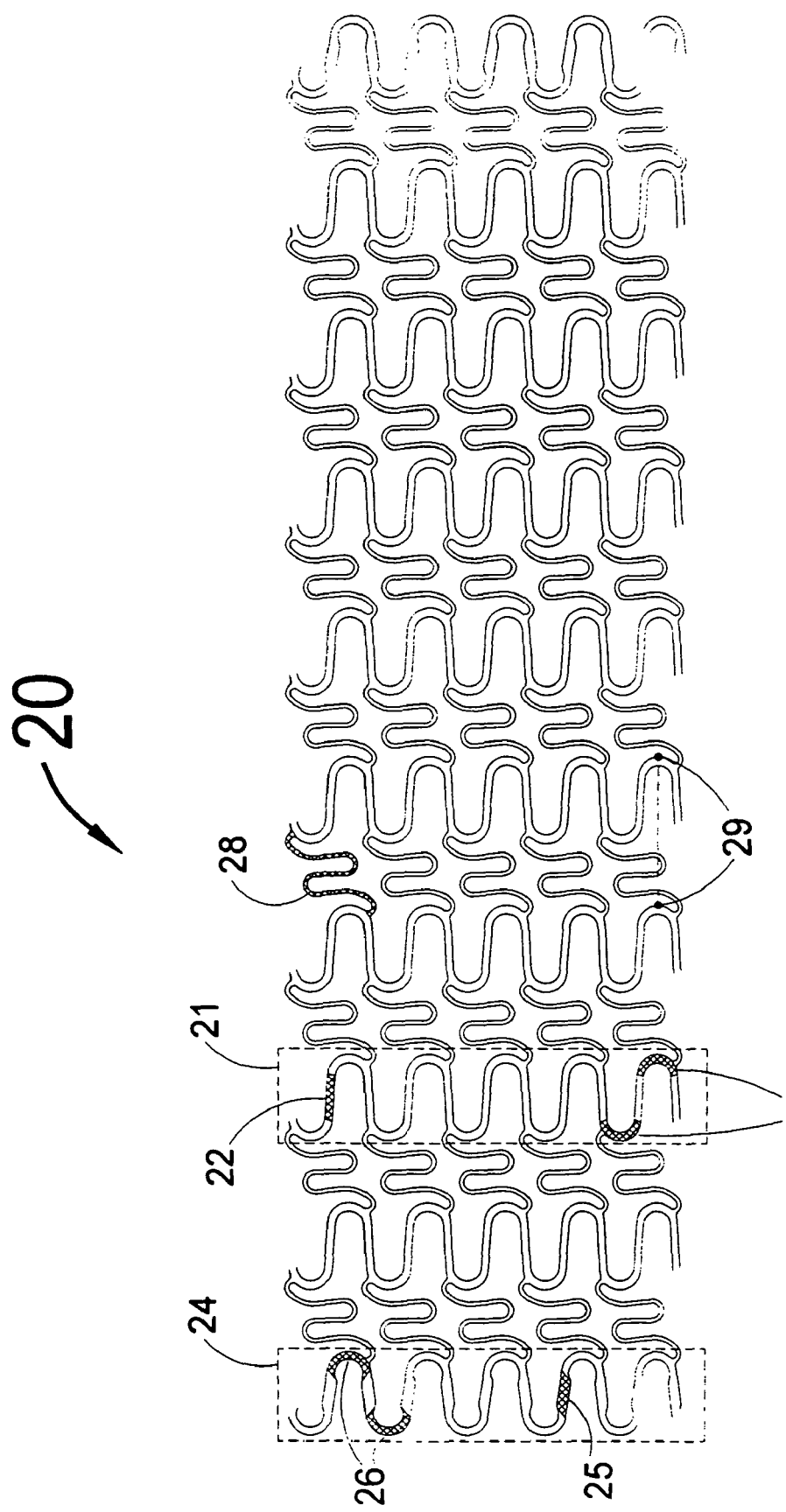

STENT WITH DIAGONAL FLEXIBLE CONNECTING LINKS

FIELD OF USE

This invention is in the field of stents for implantation into a vessel of a human body.

BACKGROUND OF THE INVENTION

Stents are well known medical devices that are used for maintaining the patency of a large variety of lumens of the human body. The most frequent use is for implantation into the coronary vasculature. Stents have been used for this purpose for almost twenty years. Some current stent designs such as the CORDIS BX Velocity™ stent have the required flexibility and radial rigidity to provide excellent clinical results. Yet sometimes such stents are not able to be delivered through extremely tortuous or highly calcified vessels.

Many current tubular stents use a multiplicity of circumferential sets of strut members connected by either straight longitudinal connecting links or undulating longitudinal (flexible) connecting links. The circumferential sets of strut members are typically formed from a series of diagonal sections connected to curved sections forming a closed-ring, generally slotted structure. This structure expands radially outwardly as the balloon on which the stent is mounted is inflated to form the element in the stent that provides structural support for the arterial wall.

A closed-cell stent is sometimes considered a stent in which (except at the longitudinal ends of the stent) every curved section of each central circumferential set of strut members has a connection to one end of a flexible link leaving no "unconnected" central curved sections. A stent with to more than half of its central (non-end) curved sections "unconnected" can be considered to be an "open-cell" stent. A hybrid design stent is one that has fewer than half or exactly half of its central curved sections being "unconnected".

SUMMARY OF THE INVENTION

The present invention envisions an improved flexible connecting link used in conjunction with in-phase and half-phase circumferential sets of strut members. The definitions of "in-phase" and "half-phase" which describe the orientation of adjacent circumferential sets of strut members will be given in the detailed description of the invention with the aid of several of the figures. By increasing the total length and diagonalness of the undulating connecting links, the present invention is a stent that provides increased flexibility during delivery and enhanced conformability to the shape of a curved artery when the stent is deployed into a curved vessel such as a tortuous coronary artery. By "increasing diagonalness" is meant that the end points of the flexible connecting links have an increased circumferential displacement each one from the other. That is, more diagonalness means that a line connecting the end points of a flexible links has an increased acute angle relative to a line that lies parallel to the stent's longitudinal axis.

The BX Velocity stent uses a balloon in which the folds are straight wrapped, to prevent the stent from twisting in a helical manner during deployment. By "straight wrapped" is meant the fold lines of the balloon lie generally parallel to the stent's longitudinal axis. Such helical twisting can result in significant foreshortening the stent. The present invention stent system envisions use is of a helically wrapped balloon. By "helically wrapped" is meant that the folds of the balloon lie at an acute angle relative to a line that is parallel to the stent's longitudinal axis. When properly oriented relative to the stent, a helically wrapped balloon can cause the stent to lengthen when the balloon is inflated as compared to a foreshortening that can occur when the stent is deployed from a straight wrapped balloon.

Three embodiments of the present invention stent are disclosed herein. Two are closed-cell stent embodiments and one is an open-cell stent embodiment. The first closed-cell stent embodiment uses "N" shaped flexible links to connect the ends of the curved sections of adjacent in-phase circumferential sets of strut members. The second closed-cell stent embodiment includes at least one end-to-end spine wherein the diagonal "N" flexible links connect from the outside of the curved sections of one circumferential set of strut members to the inside of the curved sections of the adjacent circumferential set of strut members. The spine embodiments also utilize "in-phase" circumferential sets of strut members.

The open-cell stent embodiment of the present invention stent uses diagonal "N" flexible links to connect adjacent circumferential sets of strut members where only half of the curved sections are connected by a flexible link. The unconnected crowns have shorter diagonal segments so as to reduce the potential for fish-scaling during stent delivery around a bend. "Fish-scaling" is defined as the tendency of metal struts of a stent to protrude outwardly from the surface of the balloon (like a fish scale) when the pre-deployed stent is advanced through a curved coronary artery.

Although the present invention describes in-phase circumferential sets of strut members where the diagonal flexible links span one-half cycle of circumferential displacement, it is also envisioned that flexible links spanning ⅛ to 1½ cycles are also possible. These configurations of the stents will be described in detail in the detailed description of the invention with the aid of the appropriate drawings.

It is also envisioned that any of the stent designs as taught herein may be used with plastic coatings such as parylene, antithrombogenic coatings such as heparin or phosphorylcholine or anti-restenosis coatings such as paclitaxel or sirolimus.

An additional version of the non-spined, closed-cell embodiment includes two additional configurations. The first of these concepts is a specific technique for widening the diagonal sections within a circumferential set of strut members. It is desirable to taper the diagonal sections to be wider at their center, especially for the end circumferential sets of strut members. Such widening of the diagonal sections of each end circumferential set of strut members will increase the visibility of the stent ends under fluoroscopy. If the diagonal section is widened too close to the point where a curved section connects to a diagonal section of a circumferential set of strut members, this configuration will negatively affect the unbending of the curved section as the stent is deployed. This is a result of creating unwanted plastic strain in the metal if the widened region of the diagonal section is too close to the attachment point of that diagonal section to the curved section. The present invention envisions having a strut segment of uniform width for at least approximately 0.001" between the end point of the curved section and the start of the widened taper in the diagonal section. A distance of approximately 0.002" to 0.0003" is more optimum.

The second of these concepts relates to the longitudinal spacing (i.e., the "gap") between adjacent circumferential sets of strut members. The end structure of a stent is critical to stent deliverability as the leading edge of the stent must bend first as the stent mounted onto the deployment balloon is advanced through a curved artery. Assuming the flexible links for a stent are optimized to be as long and as thin as possible within the gap allowed between adjacent circumferential sets of strut members, the only way to have increased flexibility of the end flexible links is to increase the longitudinal length of the gap between each end circumferential sets of strut members and its adjacent, central circumferential set of strut members. This increased gap will permit a longer (and more flexible) link to connect each one of the two end circumferential sets of strut members to its adjacent central circumferential set of strut members.

Thus it is an object of the present invention to have a stent with circumferential sets of strut members connected each to the other by flexible links wherein a line connecting the flexible link end points that attach to each circumferential set of strut members is diagonally oriented relative to the stent's longitudinal axis.

Another object of the present invention is to have a closed-cell stent having in-phase circumferential sets of strut members with the ends of each diagonal flexible link where they are attached to the circumferential sets of strut members being situated in close proximity to the junction point of a curved section and a diagonal section.

Still another object of the present invention is to have a stent having in-phase circumferential sets of strut members with diagonal flexible links forming an end-to-end spine to prevent stent foreshortening.

Still another object of the present invention is to have an open-cell stent having in-phase circumferential sets of strut members with diagonal flexible links wherein the ends of each diagonal flexible link are connected to the circumferential sets of strut members near the junction of a curved section and a diagonal section.

Still another object of the present invention is to have a closed-cell stent having circumferential sets of strut members with diagonal flexible links wherein the diagonal sections of at least one of the circumferential sets of strut members are tapered to be wider at their center with the taper beginning placed apart from the attachment point of the diagonal sections to the curved sections.

Still another object of the invention to have a closed-cell stent with circumferential sets of strut members connected each to the other by flexible links wherein the end diagonal flexible links are longer than the flexible links elsewhere in the stent.

These and other objects and advantages of this invention will become apparent to a person of ordinary skill in this art upon reading of the detailed description of this invention including the associated drawings.

BRIEF DESCRIPTION OF THE DRAWINGS

FIG. 2A is a flat layout view of a closed-cell embodiment of the present invention having diagonal flexible links that are connected to in-phase circumferential sets of strut members.

DETAILED DESCRIPTION OF THE INVENTION

Figure 1:
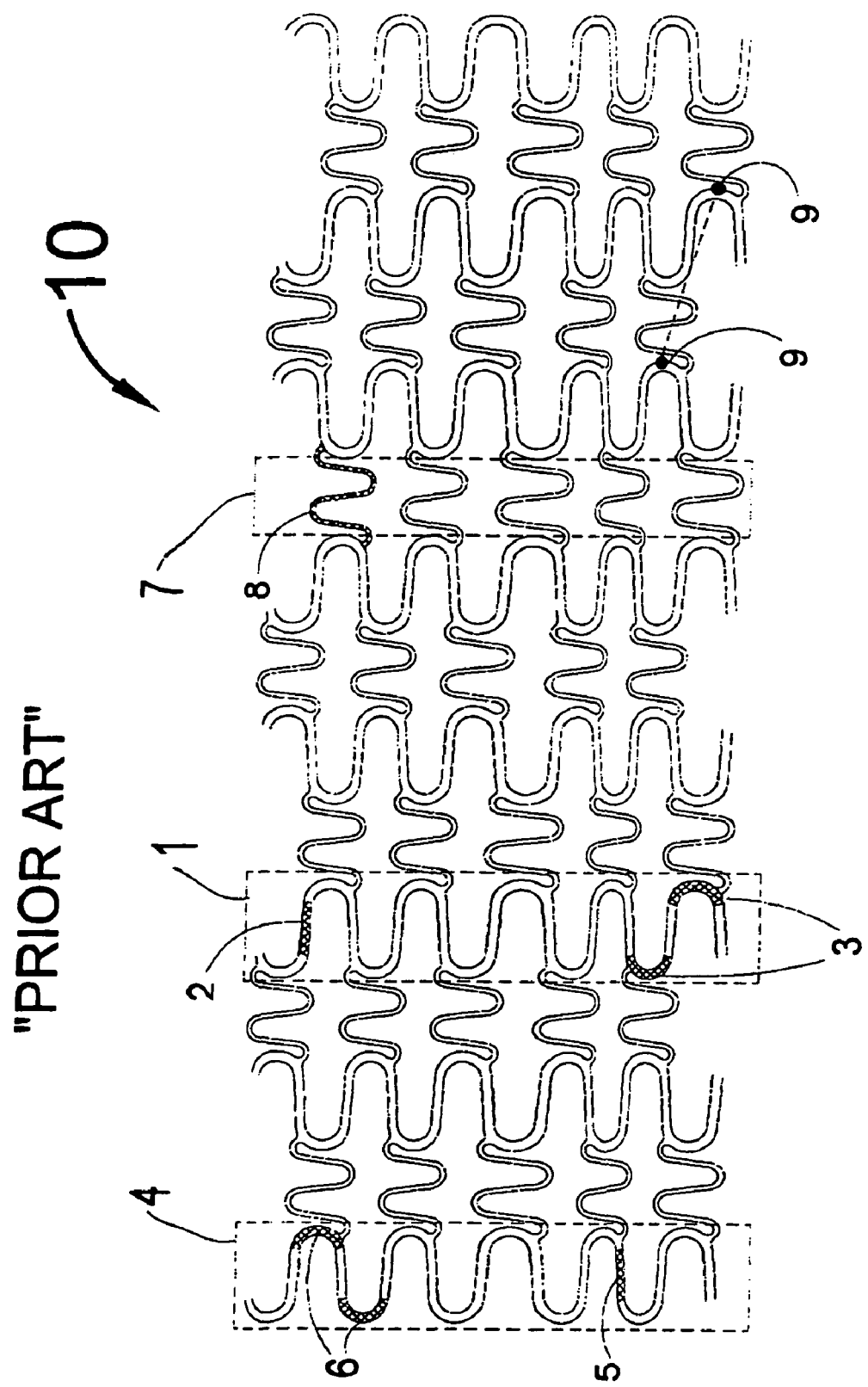
FIG. 1 is a flat layout view of a prior art stent having out-of-phase circumferential sets of strut members connected by "N" shaped flexible links.

FIG. 1 shows a flat layout view of an embodiment of a prior art closed-cell, cylindrical stent such as that described by Fischell et al in U.S. Pat. No. 6,190,403, incorporated herein by reference. The stent 10 of FIG. 1 is shown in its pre-deployed state as it would appear if it were cut longitudinally and then laid out into a flat, two-dimensional configuration. FIG. 1 is the 2-dimensional layout view that the stent 10 would have when it is crimped onto a balloon prior to the balloon being inflated to expand the stent 10 radially outward against the wall of an artery. The stent 10 has two end sets of strut members 4 and three central sets of strut members 1 that are each connected by sets of longitudinally extending, undulating "N"-shaped flexible links 8. The end sets of strut members 4 consist of alternating curved sections 6 that are attached to diagonal sections 5. The central sets of strut members 1 located longitudinally between the end sets of strut members 4 consist of alternating curved sections 3 attached to diagonal sections 2. In the prior art stent 10, the diagonal sections 5 of the end sets of strut members 4 are shorter in length than the diagonal sections 2 of the central sets of strut members 1. The shorter diagonal sections 5 will reduce the stiff longitudinal length of metal at the ends of the stent 10 to improve stent deliverability by reducing "fish-scaling". The shorter longitudinal length of the end diagonals 5 will also increase the post-expansion strength of each end set of strut members 4 as compared with the strength of each central set of strut members 6. In this prior art stent, the width of the curved sections 3 and 6 and the diagonal sections 2 and 5 are all the same. There is no variation in width within any set of strut members or between the end sets of strut members 4 and the central sets of strut members 1.

From FIG. 1 it should be noted that the flexible links 8 are designed to accommodate one another as the stent is crimped down to allow the smallest possible outside diameter of the stent 10 as it is crimped onto a delivery balloon. The flexibility of the stent 10 is dependent on the ability of the flexible links 8 to lengthen or shorten as the stent is bent through a curved artery. Analysis of flexible link flexibility has shown that increasing the circumferential extent of the "N" flexible links 8 increases the stent's flexibility. In FIG. 1, each circumferential set of strut members is circumferentially displaced each from the other by 180 degrees. This arrangement is defined as being "out-of-phase." For an out-of-phase design, the adjacent curved sections of each circumferential set of strut members is straight across from the adjacent curved section. If instead of connecting from curved sections that are straight across from each other as shown in FIG. 1, the flexible links could be connected in a more diagonal fashion, the circumferential extent of the flexible links would be longer and the stent would be more flexible.

Figure 2B:
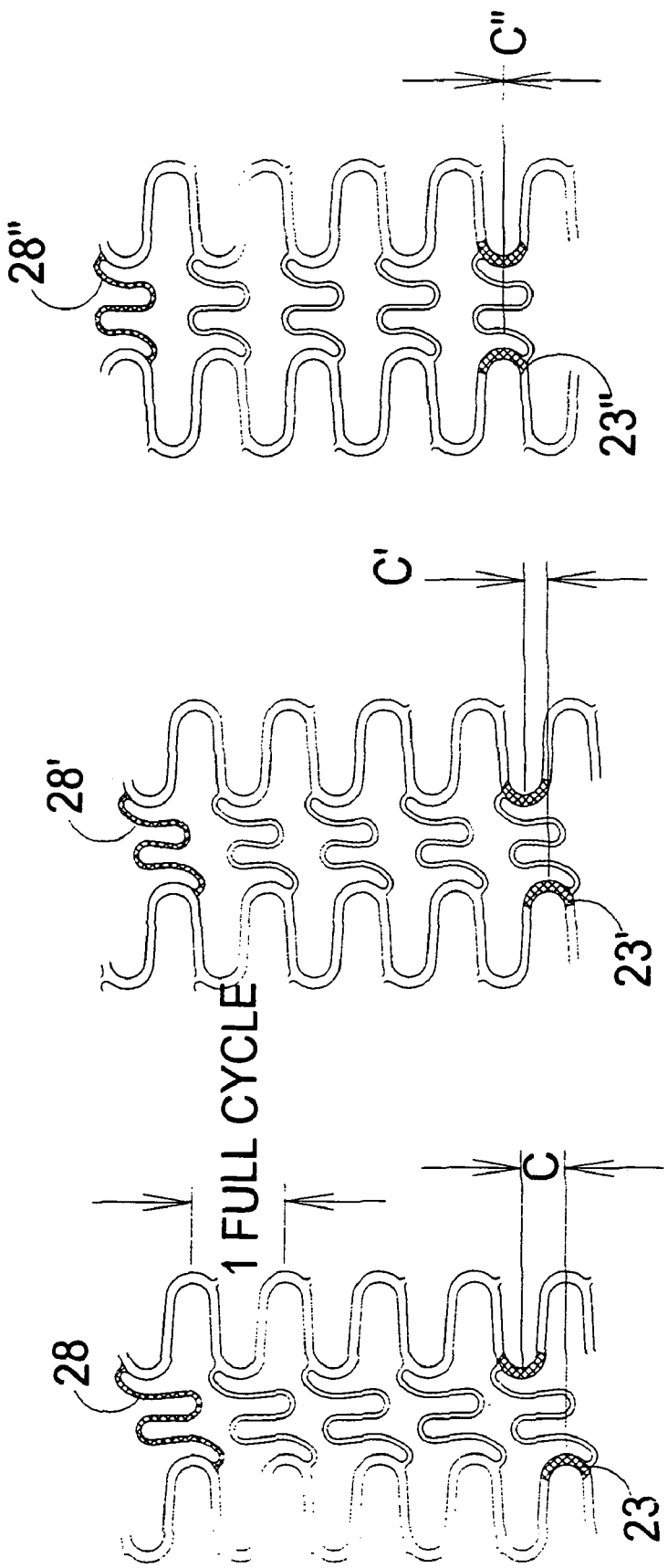
FIG. 2B are flat layout views of portions of three embodiments of the present invention showing different circumferential offsets between adjacent circumferential sets of strut members.
Figure 2C:
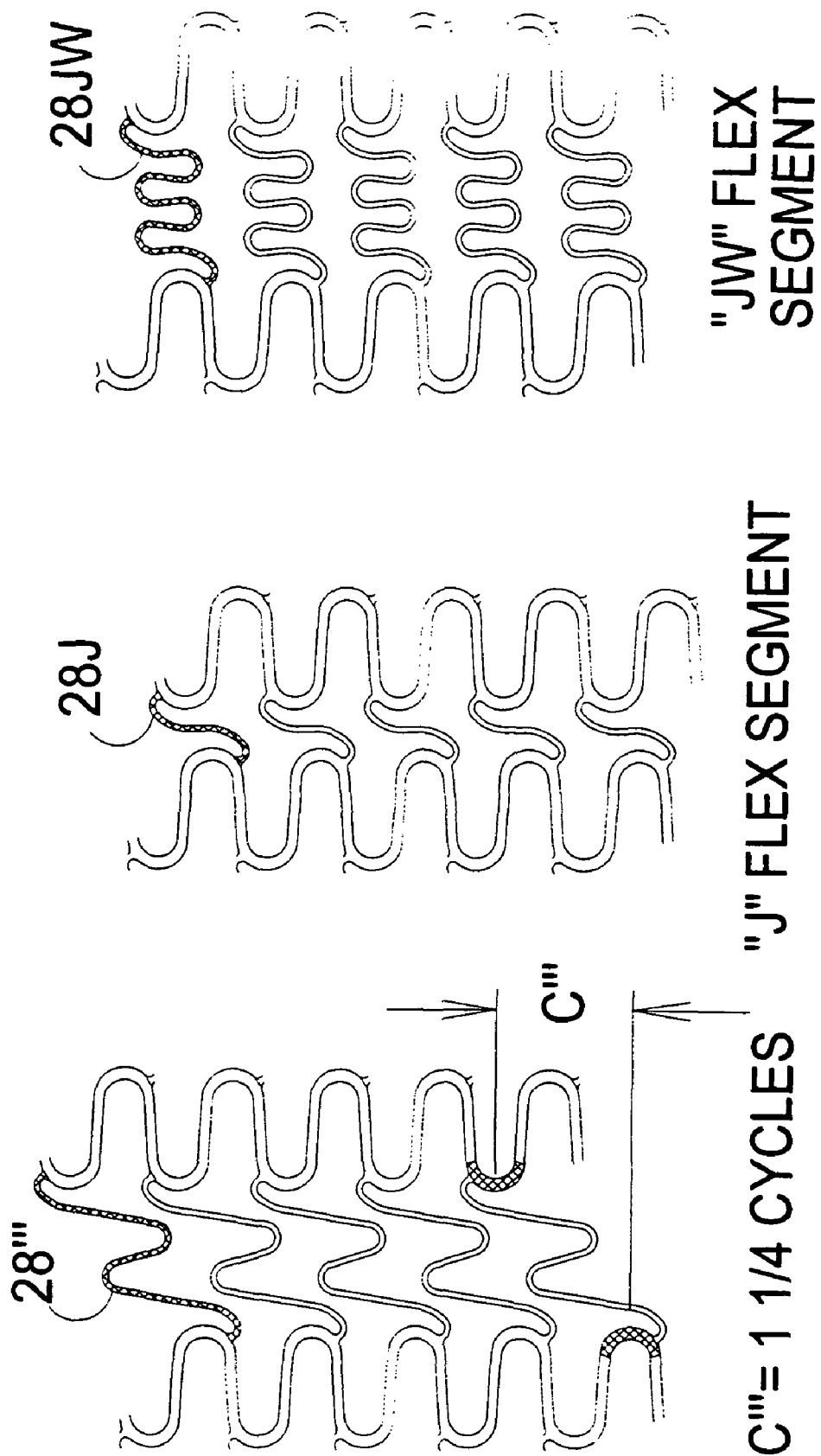
FIG. 2C are flat layout views illustrating three different types of diagonal flexible links.

FIG. 2A is a flat layout view of a closed-cell stent 20 which has diagonally connected flexible links with in-phase circumferential sets of strut members. The stent 20 is shown as cut from a metal tube before crimping the stent onto a balloon of a stent delivery system. The fact that the stent 20 that has circumferential sets of strut members that are "in-phase" is best illustrated by the orientation of a line connecting the points 29. The dotted line joining the center points 29 of the curved sections 23 or 26 that are curved in the same direction would lie essentially parallel to the longitudinal axis L of the stent 20. It can also be said that each center point 29 is not circumferentially displaced from the center point 29 of the curved section 23 or 26 of the adjacent circumferential set of strut members. It is certainly envisioned that the flexible links 8 (of FIG. 1) or 28 could be attached diagonally to opposing curved sections that are in-phase, out-of-phase, or anywhere in between these two states. It is also envisioned that the flexible links can be even more diagonally attached as illustrated by the 1¼ cycles connection as shown in FIG. 2C.

The stent 20 has end sets of strut members 24 located at each end of the stent 20 and eight central sets of strut members 21 connected each to the other by sets of longitudinally extending undulating diagonal flexible links 28. The end sets of strut members 24 consist of alternating curved sections 26 and diagonal sections 25. The central sets of strut members 21 located longitudinally between the end sets of strut members 24 consist of alternating curved sections 23 and diagonal sections 22. In the stent 20, the diagonal sections 25 of the end sets of strut members 24 are shorter and wider than the diagonal sections 22 of the central sets of strut members 21. The shorter diagonal sections 25 will reduce the stiff longitudinal length of metal at the ends of the stent 20 to improve deliverability by reducing "fish-scaling". The shorter diagonal sections 25 will also increase the post-expansion strength of the end sets of strut members 21.

The wider diagonal sections 25 of the end circumferential sets of strut members 24 enhance the radiopacity of the ends of the stent 20. This is particularly important because the interventional cardiologist who implants the stent can visualize the stent more accurately after emplacement at an arterial stenosis when there is clear visualization of the ends of the stent. In the stent 20, the width of the curved sections 23 and 26 can be tapered to improve the ratio of strength to maximum plastic strain, as described in U.S. patent application Ser. No. 09/797,641 incorporated herein by reference. The curved sections 26 or 23 that connect to the ends of the diagonal flexible links 28 are, in this embodiment, displaced circumferentially by a one-half cycle.

This relationship essentially defines the relative circumferential positions of the circumferential sets of strut members for an in-phase stent configuration. That is, FIG. 2A and the left portion of FIG. 2B show that each of the circumferential sets of strut members are "in-phase" with each other. This is contrasted with the stent 10 of FIG. 1, wherein despite the diagonal (spiral) nature of the connections of the flexible links 8, the flexible links 8 connect to opposing curved sections 3 or 6 that have a zero cycle circumferential displacement. In other words, the present invention stents are different than the prior art stent 10 of FIG. 1 where out-of-phase adjacent circumferential sets of strut members 1 and 4 are mirror images of each other. The in-phase design of the stent 20 of FIG. 2A permits more circumferential displacement of the end point connections of the flexible links 28 to the curved sections 23 or 26 as compared with the connections for the flexible links 8 of FIG. 1. This increased circumferential displacement of the connection points for the diagonal flexible links 28 makes them longer, and thus more easily stretched or compressed as the stent 20 is bent. Therefore, the stent 20 of FIG. 2A is envisioned to be more flexible than the stent 10 of FIG. 1.

The stent 20 shown in FIG. 2A has five connecting diagonal flexible links 28 between each adjacent set of circumferential sets of strut members 21 or 24. It is also envisioned that three, four, six or more than six such connecting links could also be used. The stent 20 having five flexible links is a design that is ideally suited for placement into arteries having a diameter between 2.5 and 3.5 mm. Fewer connecting links (e.g., three) with fewer cells around are typically applicable to smaller diameter vessels. Stents with more connecting links and therefore having more cells around the stent's circumference are better suited for larger vessels. This is because good scaffolding of the vessel wall is maintained when the area of each cell of the stent remains fairly constant irrespective of the stent's final diameter when expanded against the arterial wall. Thus larger diameter stents require more cells around the stent's circumference as compared to smaller diameter stents that have fewer cells around.

Although the in-phase circumferential sets of strut members 21 and 24 of the stent 20 create a one-half cycle additional circumferential displacement of the diagonal flexible links 28 as compared with the flexible links 8 of FIG. 1, it is envisioned that circumferential displacements of one-eighth cycle or more can achieve improvement in stent flexibility through an increase in the circumferential extent of the diagonal flexible links 28. FIG. 2B illustrates ¼, ½ and 0 cycle circumferential displacements of the adjacent circumferential sets of strut members. It should be understood that any circumferential displacement of the circumferential sets of strut members that lies between in-phase and out-of-phase is envisioned. Even circumferential displacements greater than ½ cycle (e.g., ¾ cycle) are also envisioned. A probable maximum circumferential displacement for the flexible link connection points is 1¼ cycles as shown to the left in FIG. 2C.

FIG. 2B shows alternate embodiments of the stent 20 of FIG. 2A. The stent portion on the left that is labeled C=½ CYCLE shows the ½ cycle circumferential offset of the curved sections 23 at each end of a diagonal flexible link 28. This is identical to the stent design shown in FIG. 2A. The stent portion at the center of FIG. 2B labeled C'=¼ CYCLE shows the ¼ cycle circumferential offset of the curved sections 23' that are joined by the diagonal flexible links 28'. The stent portion on the right that is labeled C"=0 CYCLE is identical to the prior art stent shown as stent 10 of FIG. 1. This 0 CYCLE is an out-of-phase design stent having curved sections 23" attached to flexible links 28".

FIG. 2C illustrates other variations for flexible links connected to adjacent circumferential sets of strut members. Specifically, the left part of FIG. 2C shows a C'=1¼ CYCLES with a very large circumferential displacement for the end points of the flexible links 28'. The center portion of FIG. 2C shows a "J" type flexible link 28J which also can be used for connecting adjacent circumferential sets of strut members. The right portion of FIG. 2C shows a very undulating form of flexible connector 28JW which would impart a high degree of flexibility to the stent. Any of these flexible links could be designed to impart more or less flexibility to various portions of a stent.

Figure 3:
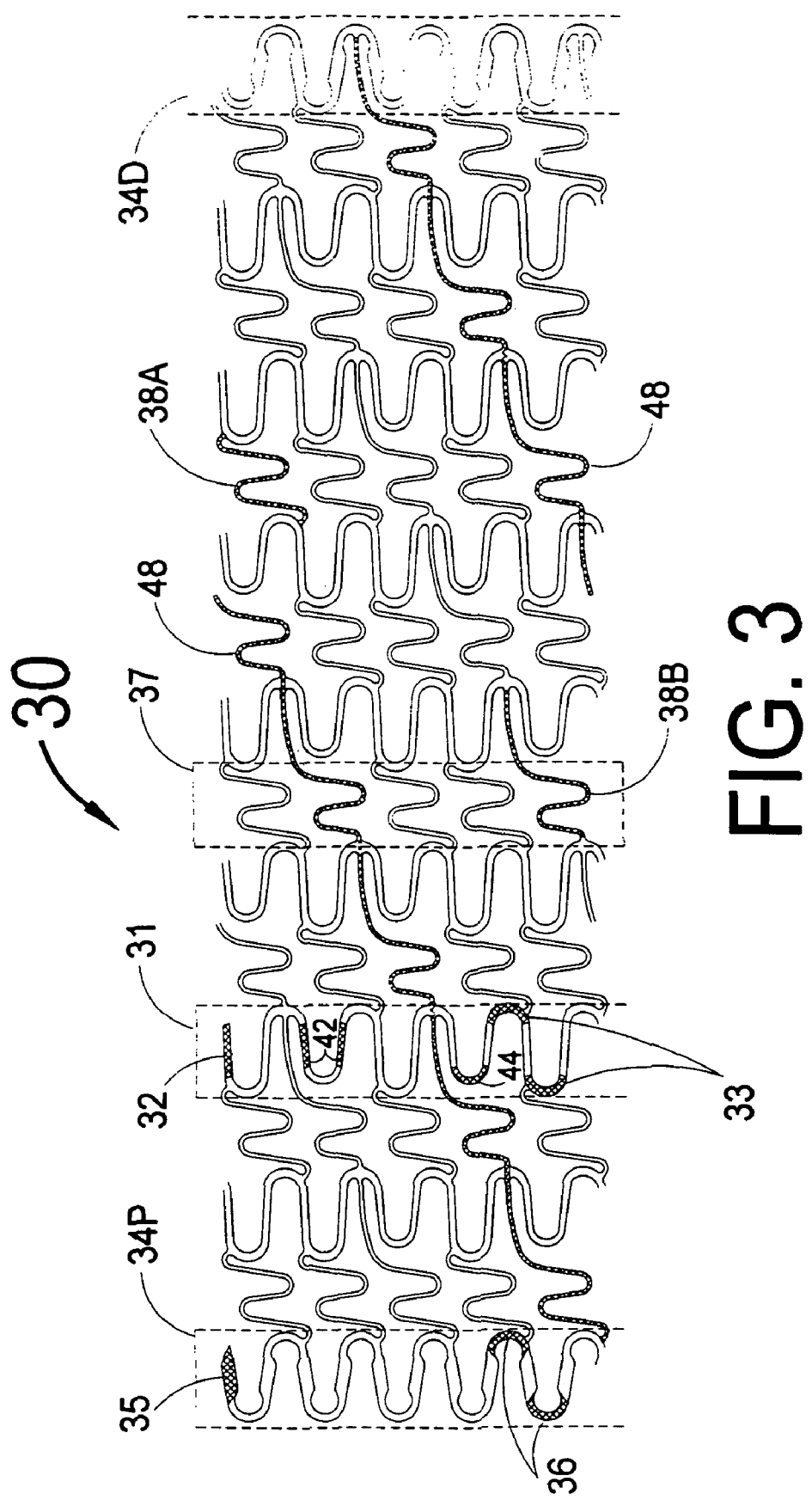
FIG. 3 is a flat layout view of an embodiment of the present invention having diagonal flexible links, in-phase circumferential sets of strut members and also having two end-to-end spines to reduce stent foreshortening.

FIG. 3 shows a stent 30 that is another embodiment of the present invention using diagonally connected "N" flexible links. The stent 30 has two end-to-end spines 48 that will reduce foreshortening when such a stent is expanded against a vessel wall. The stent 30 is, in most other ways, similar to the stent 20 of FIG. 2 in that the central and end circumferential sets of strut members 31, 34P and 34D of the stent 30 are "in-phase." The stent 30 of FIG. 3 is shown in its pre-deployed state before crimping onto a balloon. FIG. 3 shows the stent 30 as it would appear if it were cut longitudinally and then laid out into a flat, 2-dimensional configuration. The stent 30 has end sets of strut members 34P and 34D located respectively at the proximal and distal ends of the stent 30 and seven central sets of strut members 31 connected each to the other by sets of longitudinally extending, undulating, diagonally connected flexible links 38A and 38B.

The end sets of strut members 34P and 34D consist of alternating curved sections 36 attached to widened diagonal sections 35. The central sets of strut members 31 located longitudinally between the end sets of strut members 34P and 34D consist of curved sections 33 and 44 and diagonal sections 32 and 42. In the stent 30, the diagonal sections 35 of the end sets of strut members 34P and 34D are wider than the diagonal sections 32 and 42 of the central sets of strut members 21. The wider diagonal sections 35 of the end circumferential sets of strut members 34P and 34D enhance the radiopacity of the ends of the stent 30. In the stent 30, the width of the curved sections 33 and 36 may be tapered to improve the ratio of radial strength to maximum plastic strain when the stent is expanded.

The flexible links 38A connect between the outside of curved sections 36 or 33 of adjacent circumferential sets of strut members 34P, 34D or 31 while the flexible links 38B connect between the outside of one curved section 36 or 33 and the inside of a curved section 33 or 36 of the adjacent circumferential set of strut members. The flexible links 38B form most of the spines 48 that run the length of the stent 30. One key feature of the stent 30 is that the outside of every distally extending curved section 36 or 33 is attached to a flexible link. This will reduce the extent of fish-scaling of the stent 30 as the stent is advanced in a forward (i.e., distal) direction. As seen in FIG. 3, the diagonal sections 42 that attach to the unconnected curved sections 44 are shorter that the diagonal sections 32 that connect to connected curved sections 33 of the central circumferential sets of strut members 31. Because these diagonals 42 that attach to the unconnected curved sections 44 are shorter, the potential for fish-scaling when the stent is pulled back in the proximal direction is reduced.

Figure 4:
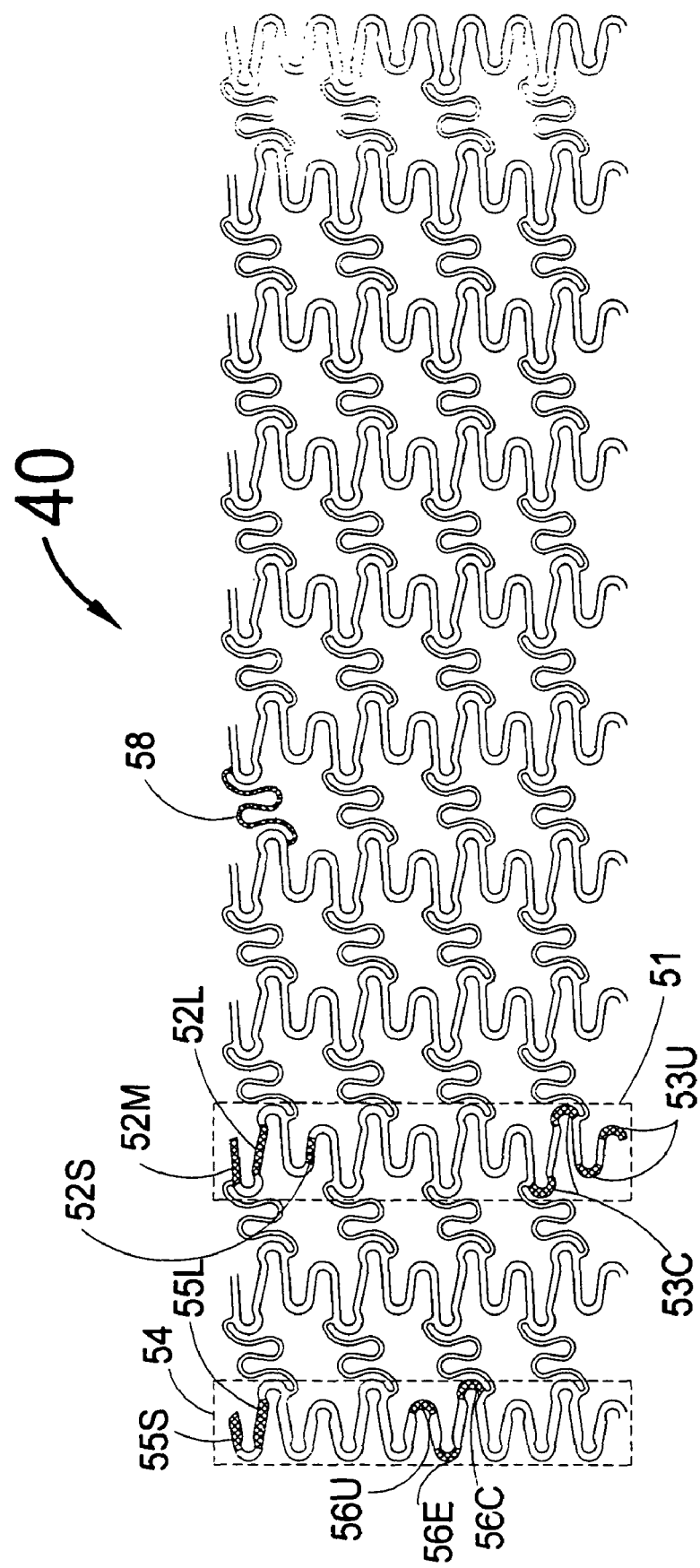
FIG. 4 is a flat layout view of an open-cell embodiment of the present invention having diagonal flexible links with in-phase circumferential sets of strut members.

FIG. 4 shows an open-cell alternative embodiment of the present invention that also has diagonal flexible links. The stent 40 of FIG. 4 is shown in its layout state as it would appear if it were cut longitudinally and then laid out into a flat, 2-dimensional configuration. As with the stents of FIGS. 2 and 3, FIG. 4 illustrates a 2-dimensional view of how the cylindrical stent 40 would look after it is cut out of thin-walled metal tube before it is crimped onto a balloon of a stent delivery system. The stent 40 comprises end sets of strut members 54 located at each end of the stent 40 and eight central sets of strut members 51 connected each to the other by sets of longitudinally extending, undulating, diagonal flexible links 58. The end sets of strut members 54 consist of alternating curved sections 56E, 56U and 56C with diagonal sections 55S and 55L. The curved sections 56E are located on the actual ends of the stent 40. The curved sections 56U and 56C are so designated because the curved sections 56C are connected to diagonal flexible links 58 while the curved sections 56U are unconnected. The unconnected curved sections 56U attach to shorter end diagonal sections 55S than the connected curved sections 56C that connect to the longer end diagonal sections 55L. The central sets of strut members 51 located longitudinally between the end sets of strut members 54 consist of alternating curved sections 53C and 53U with diagonal sections 52S, 52M and 52L. The curved sections 53U and 53C are so designated because the curved sections 53C are connected to diagonal flexible links 58 while the curved sections 53U are unconnected. The unconnected curved sections 53U attach to the shortest central diagonal section 52S while the connected curved sections 53C connect to the longer central diagonal sections 52M and 52L. The advantage of having the unconnected curved sections 56U and 53U attach to shortest diagonal sections 55S and 52S is that, as the stent 40 is delivered mounted onto a delivery balloon into a curved vessel, any unconnected portion of the stent 40 can protrude outward from the balloon on which it is mounted. Thus unconnected curved sections, such as curved sections 56U and 53U could be caught on tight vessel blockages or on the arterial wall as the stent is advanced through curved arteries. Because the diagonal sections 55S and 52S are short, the extent of this phenomena called "fish scaling" is minimized.

In the stent 40, the diagonal sections 55S and 55L of the end sets of strut members 54 are wider than the diagonal sections 52S, 52M and 52L of the central sets of strut members 51. The wider diagonal sections 55S and 55L of the end circumferential sets of strut members 54 enhance the radiopacity of the ends of the stent 40 where it is most important. In the stent 40, the width of the curved sections 53C, 53U, 56E, 56C and 56U may be tapered to improve the ratio of strength to maximum plastic strain. The central and end circumferential sets of strut members 51 and 54 of the stent 20 are "in-phase." The in-phase design of the stent 40 of FIG. 4 permits more circumferential displacement for the attachment points for the flexible links 58 as compared to the stent 10 shown in FIG. 1. The increased circumferential displacement of the diagonal flexible links 58 makes them longer and thus more easily stretched or compressed as the stent 40 is advanced through highly curved arteries. This enhances the flexibility and hence the deliverability of the stent 40.

The open-cell stent 40 shown in FIG. 4 has four connecting diagonal flexible links 58 between each adjacent circumferential set of strut members. It is also envisioned that three, five, six or more such connecting links could also be used. Typically, the greater the diameter of the deployed stent, the greater would be the number of flexible links between each adjacent circumferential set of strut members.

Figure 5:
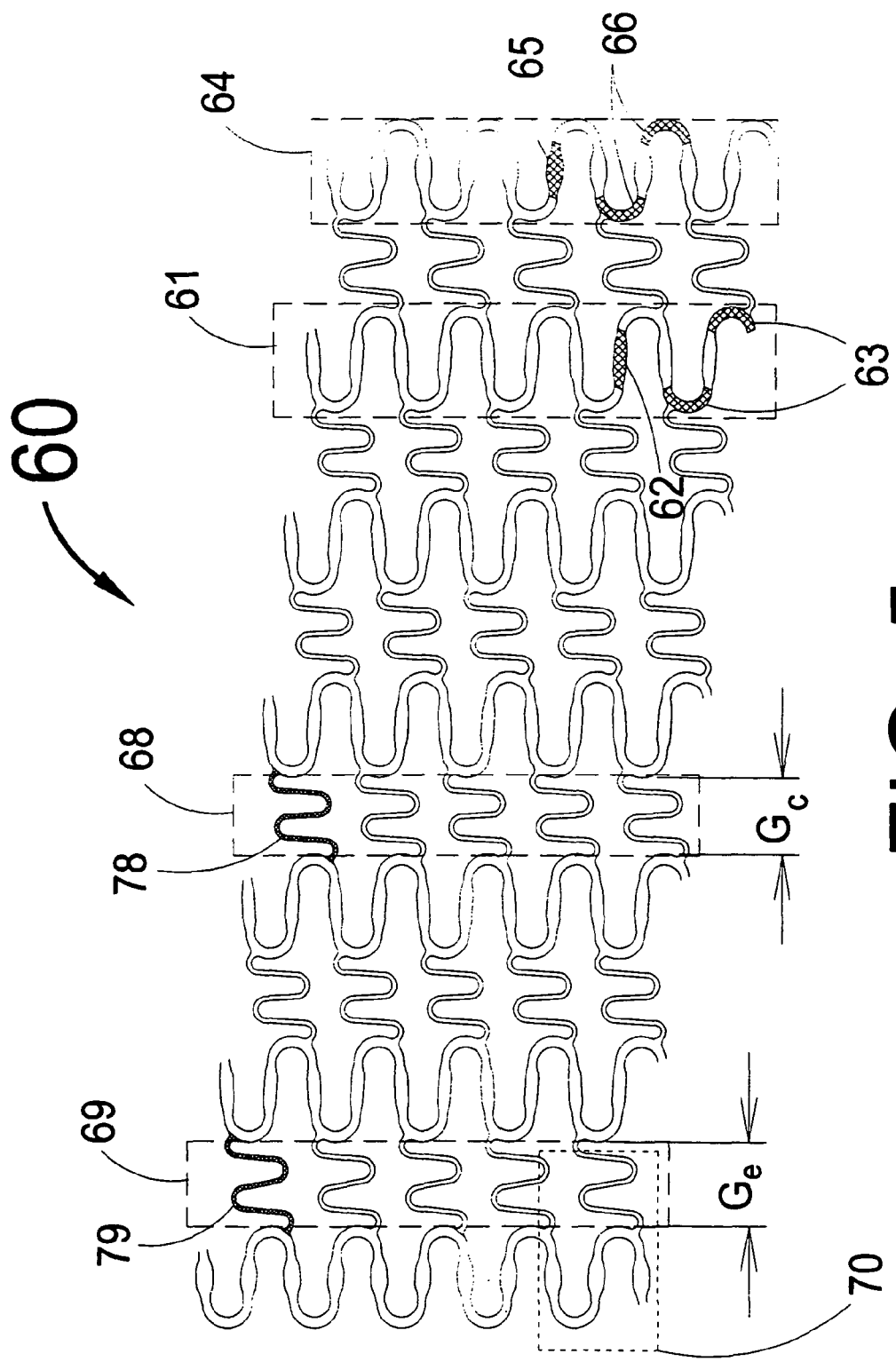
FIG. 5 is a flat layout view of an alternative closed-cell embodiment of the present invention having circumferential sets of strut members with a ¼ cycle (half-phase) circumferential offset.

The stent 60 of FIG. 5 is shown in its pre-crimped state as it would appear if it were cut longitudinally and then laid out into a flat, 2-dimensional configuration. The stent 60 has end sets of strut members 64 located at each end of the stent 60 and five central sets of strut members 61 connected each to the other by sets of flexible links 68 and 69; each set comprising 5 individual flexible links 78 or 79. The end flexible links 79 that connect adjacent circumferential sets of strut members at the ends of the stent 60 are longer than the central flexible links 78 connecting all other adjacent circumferential sets of strut members. This increased length is possible because of the increased longitudinal gap $G_e$ between the adjacent circumferential sets of strut members at the end of the stent as compared with the gap $G_c$ between all central circumferential sets of strut members 61. The increased length of the end flexible links 79 increases the flexibility at the ends of the stent during deployment in curved vessels. The shorter gap $G_c$ will place the central circumferential sets of strut members 61 closer together thereby increasing the stent's radial strength where there is the highest plaque burden in a dilated arterial stenosis.

The end sets of strut members 64 consist of alternating curved sections 66 and diagonal sections 65. The central sets of strut members 61 located longitudinally between the end sets of strut members 64 consist of alternating curved sections 63 and diagonal sections 62. In the stent 60, the diagonal sections 65 of the end sets of strut members 64 are shorter and tapered to be wider than the diagonal sections 62 of the central sets of strut members 61. The shorter diagonal sections 65 will reduce the stiff longitudinal length of metal at the ends of the stent 60 to improve deliverability. The wider diagonal sections 65 of the end circumferential sets of strut members 64 enhance the radiopacity of the ends of the stent 60 where it is most important for accurate placement of the stent relative to a stenosis that is being dilated by the stent. In the stent 60, the width of the curved sections 63 and 66 may be tapered to improve the ratio of strength to maximum allowed plastic strain. The curved sections 66 or 63 that connect to the ends of the diagonal flexible links 79 and 78 are, in this embodiment, displaced circumferentially by a one-quarter cycle. This is the same as the central portion of FIG. 2B and is defined as a "half-phase" orientation of the circumferential sets of strut members. "Half-phase" is appropriate nomenclature because one-quarter cycle is half way between an in-phase configuration and an out-of-phase configuration.

Figure 6:
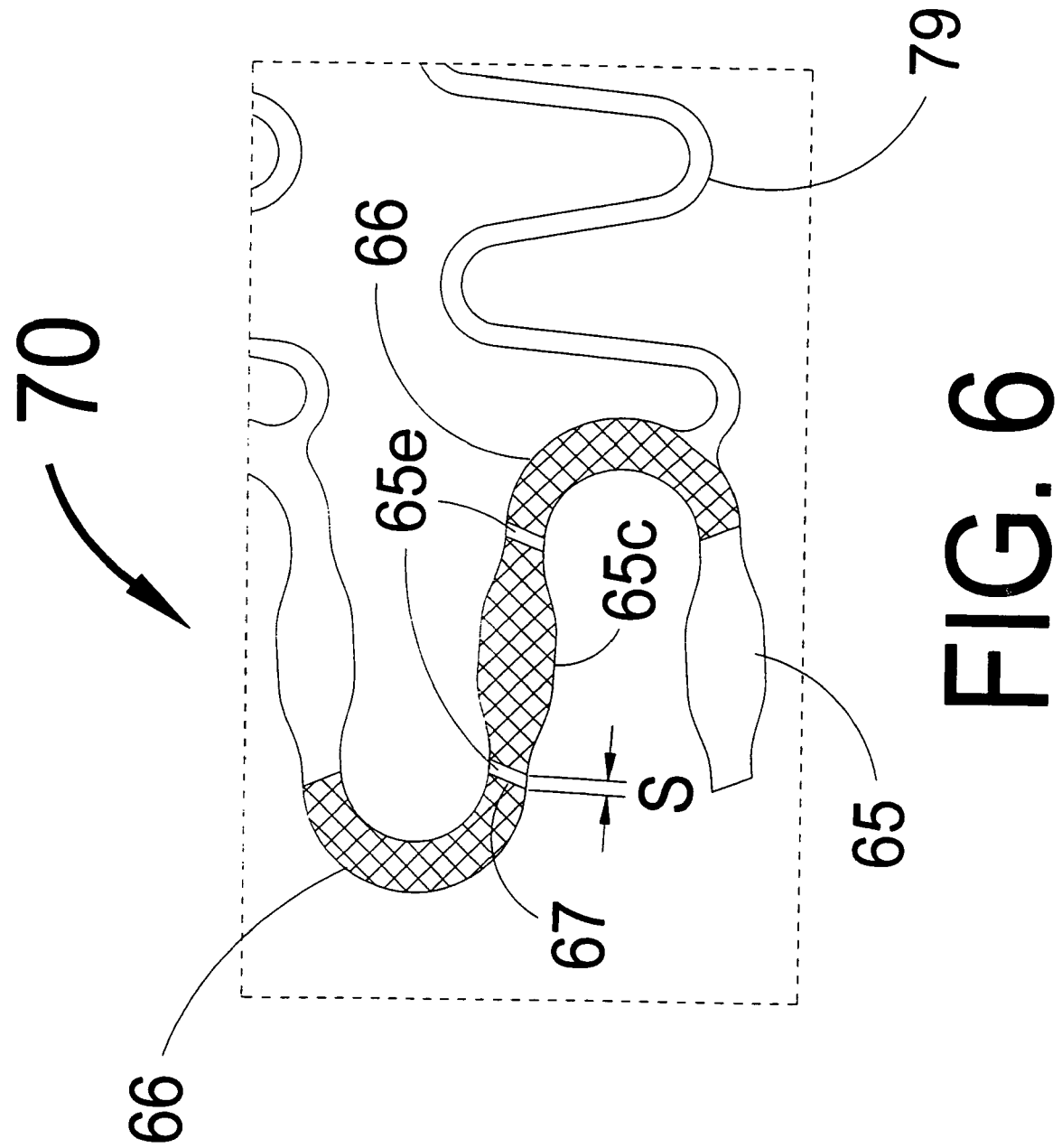
FIG. 6 is an enlargement of the area 70 of the stent of FIG. 5.

The end circumferential sets of strut members 64 have tapered diagonal sections 65. The tapered diagonal sections 65 and 62 are wider at their center. FIG. 6 is an enlargement of the area 70 of the stent 60 of FIG. 5. As seen more clearly in FIG. 6, the tapered diagonal section 65 has end straight sections 65e and central tapered sections 65c. The tapered section 65c begins a distance S from the attachment point 67 of the diagonal section 65 to the curved section 66. The regions 65e have a uniform strut width as opposed to a changing strut width of the diagonal section 65c and the curved section 66. The length "S" of uniform strut width should be approximately between 0.0001" and 0.0003".

Various other modifications, adaptations, and alternative designs are of course possible in light of the above teachings. Therefore, it should be understood at this time that within the scope of the appended claims the invention may be practiced otherwise than as specifically described herein.

What is claimed is:

1. A stent in the form of a multi-cellular, tubular structure having a longitudinal axis, the stent structure including:
a plurality of sets of cylindrical strut members with each circumferential set of strut members consisting of a multiplicity of curved sections attached end-to-end to diagonal sections to form a closed, ring-like structure circumferentially situated around the stent's longitudinal axis, one of the sets of strut members being located at each end of the stent, the struts in a set of cylindrical struts having a thickness in the circumferential direction and the end set of strut members being greater in thickness than each of the central circumferential sets of strut members located apart from each end; each circumferential set of strut members being longitudinally separated from an adjacent circumferential set of strut members and each circumferential set of strut members also being circumferentially displaced by between about one-eighth and about one-quarter cycle from the adjacent circumferential set of strut members; and
at least one diagonal flexible link joining each pair of adjacent circumferential sets of strut members with each diagonal flexible link having a first end that is fixedly attached at a first attachment point to a curved section of one circumferential set of strut members and a second end that is fixedly attached at a second attachment point to a curved section of an adjacent circumferential set of strut members, the first attachment point being circumferentially displaced from the second attachment point by at least a half cycle of the circumferential sets of strut members.

2. The stent of claim 1 wherein the shape of at least one of the diagonal flexible links is selected from a group that includes "N" shaped links, inverted "N" shaped links, "J" shaped links and "JW" shaped links with each of the "N" link or inverted "N" link having at least four generally longitudinal extending curved segments, each "J" link having two generally longitudinally extending curved segments, and each "JW" link having six generally longitudinally extending curved segments.

3. The stent of claim 1 wherein at least one-half of the curved sections of each central circumferential set of strut members are connected by diagonal flexible links.

4. The stent of claim 1 wherein every curved section of each central circumferential set of strut members is connected to a diagonal flexible link.

5. The stent of claim 1 wherein the circumferential displacement of the two attachment points for each diagonal flexible link is at least one full cycle of the circumferential sets of strut members.

6. A stent in the form of a multi-cellular, tubular structure having a longitudinal axis, the stent structure including:
a plurality of sets of cylindrical strut members with each circumferential set of strut members consisting of a multiplicity of curved sections attached end-to-end to diagonal sections to form a closed, ring-like structure circumferentially situated around the stent's longitudinal axis, one of the sets of strut members being located at each end of the stent, the struts in a set of cylindrical struts having a thickness in the circumferential direction and the end set of strut members being greater in thickness than each of the central circumferential sets of strut members located apart from each end; each end circumferential set of strut members being longitudinally separated from an adjacent circumferential set of strut members by a greater length as compared to the longitudinal separation between adjacent central circumferential set of strut members and between about one-eighth and about one-quarter of a cycle in the circumferential direction for an adjacent set of strut members; and
at least one diagonal flexible link joining each pair of adjacent circumferential sets of strut members with each diagonal flexible link having a first end that is fixedly attached at a first attachment point to a curved section of one circumferential set of strut members and a second end that is fixedly attached at a second attachment point to a curved section of an adjacent circumferential set of strut members, the length of any diagonal flexible link joined to a curved section of an end circumferential set of strut members being longer than the length of any diagonal flexible link that joins any pair of adjacent central circumferential sets of strut members.

7. A stent in the form of a multi-cellular, tubular structure having a longitudinal axis, the stent structure including:
a plurality of sets of cylindrical strut members with each circumferential set of strut members consisting of a multiplicity of curved sections with each curved section being connected at a point of attachment to a diagonal section to form a closed, ring-like structure circumferentially situated around the stent's longitudinal axis, one of the sets of strut members being located at each end of the stent, the struts in a set of cylindrical struts having a thickness in the circumferential direction and the end set of strut members being greater in thickness than each of the central circumferential sets of strut members located apart from each end; each circumferential set of strut members being longitudinally separated from an adjacent circumferential set of strut members and each circumferential set of strut members also being circumferentially displaced by between about one-eighth and about one-quarter cycle from the adjacent circumferential set of strut members and at least one diagonal section being tapered to be widest at its center; and at least one diagonal flexible link joining each pair of adjacent circumferential sets of strut members with each diagonal flexible link having a first end that is fixedly attached at a first attachment point to a curved section of one circumferential set of strut members and a second end that is fixedly attached at a second attachment point to a curved section of an adjacent circumferential set of strut members, the first attachment point being circumferentially displaced from the second attachment point by at least one-eighth of a cycle of the circumferential sets of strut members.

8. The stent of claim 7 wherein the taper in the at least one diagonal section that is tapered begins at a distance between approximately 0.001 and 0.003 inches from the point of attachment of a curved section to a diagonal section.

9. A stent in the form of a multi-cellular, tubular structure having a longitudinal axis, the stent structure including:
- a plurality of sets of cylindrical strut members with each circumferential set of strut members consisting of a multiplicity of curved sections attached end-to-end to diagonal sections to form a closed, ring-like structure circumferentially situated around the stent's longitudinal axis, one of the sets of strut members being located at each end of the stent, the struts in a set of cylindrical struts having a thickness in the circumferential direction and the end set of strut members being greater in thickness than each of the central circumferential sets of strut members located apart from each end; each circumferential set of strut members being longitudinally separated from an adjacent circumferential set of strut members with the longitudinal separation length between the end circumferential set of strut members and the adjacent central circumferential set of strut members being longer than the separation length of adjacent central circumferential sets of strut members and between about one-eighth and about one-quarter of a cycle in the circumferential direction for an adjacent set of strut members; and
- at least one diagonal flexible link joining each pair of adjacent circumferential sets of strut members with each diagonal flexible link connecting to an end circumferential set of strut members having a greater length as compared to the length of any diagonal flexible link that connects adjacent central circumferential sets of strut members thereby increasing the flexibility at each end of the stent.

10. A stent in the form of a multi-cellular, tubular structure having a longitudinal axis, the stent structure including:
- a plurality of sets of cylindrical strut members with each circumferential set of strut members consisting of a multiplicity of curved sections attached end-to-end to diagonal sections to form a closed, ring-like structure circumferentially situated around the stent's longitudinal axis, one of the sets of strut members being located at each end of the stent, the struts in a set of cylindrical struts having a thickness in the circumferential direction and the end set of strut members being greater in thickness than each of the central circumferential sets of strut members located apart from each end; each circumferential set of strut members being longitudinally separated from an adjacent circumferential set of strut members and each circumferential set of strut members also being circumferentially displaced by between about one-eighth and about one-quarter cycle from the adjacent circumferential set of strut members;
- at least one diagonal flexible link joining each pair of adjacent circumferential sets of strut members with each diagonal flexible link having a first end that is fixedly attached at a first attachment point to a curved section of one circumferential set of strut members and a second end that is fixedly attached at a second attachment point to a curved section of an adjacent circumferential set of strut members, the first attachment point being circumferentially displaced from the second attachment point by at least a half cycle of the circumferential sets of strut members; and
- at least one row of spines extending for the entire longitudinal length of the stent, the at least one row of spines consisting of a serially connected diagonal flexible links joined from the outer curvature of one curved section to the inner curvature of a curved section of an adjacent circumferential set of strut members.

11. A cylindrical stent having a longitudinal axis and comprising:
- sets of cylindrical strut members consisting of a multiplicity of curved sections attached end-to-end to diagonal sections to form a closed, ring-like structure one of the sets of strut members being located at each end of the stent, the struts in a set of cylindrical struts having a thickness in the circumferential direction and the end set of strut members being greater in thickness than each of the central circumferential sets of strut members located apart from each end; each circumferential set of strut members being longitudinally separated and circumferentially displaced by between about one-eighth and about one-quarter cycle from the adjacent circumferential set of strut members; and
- at least one diagonal flexible link joining each pair of adjacent circumferential sets of strut members.

* * * * *